United States Patent
Thompson

(10) Patent No.: US 12,264,329 B1
(45) Date of Patent: Apr. 1, 2025

(54) COMPOSITION FOR REGULATING PRODUCTION OF FUSION PROTEINS

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/738,959

(22) Filed: Jun. 10, 2024

(51) Int. Cl.
*A61K 48/00* (2006.01)
*C07K 14/705* (2006.01)
*C12N 15/13* (2006.01)
*C12N 15/62* (2006.01)
*C12N 15/86* (2006.01)
*C12N 15/864* (2006.01)
*A61K 38/00* (2006.01)

(52) U.S. Cl.
CPC ............ *C12N 15/86* (2013.01); *C07K 14/705* (2013.01); *A61K 38/00* (2013.01); *C07K 2319/30* (2013.01); *C12N 2750/14143* (2013.01)

(58) Field of Classification Search
None
See application file for complete search history.

(56) References Cited

FOREIGN PATENT DOCUMENTS

| WO | WO 00/73481 | * 12/2000 |
| WO | WO 2008052043 | * 10/2007 |

* cited by examiner

*Primary Examiner* — Maria Marvich
(74) *Attorney, Agent, or Firm* — Gowling WLG (Canada) LLP

(57) ABSTRACT

Some embodiments of the present disclosure relate to one or more compositions that upregulate the production of one or more sequences of mRNA. The sequences of mRNA may encode for translation of a target biomolecule, thereby causing an increase in bioavailability of the target biomolecule within a subject that is administered the one or more compositions. In some embodiments of the present disclosure, the target biomolecule is a fusion protein with an Fc fragment, such as a mu opioid receptor-Fc (MOR-Fc) that may be biologically active in the absence of an opioid ligand.

7 Claims, No Drawings
Specification includes a Sequence Listing.

COMPOSITION FOR REGULATING PRODUCTION OF FUSION PROTEINS

This application contains a Sequence Listing electronically submitted via Patent Center to the United States Patent and Trademark Office as an XML Document file entitled "A8149550US—Sequence Listing ST26.xml" created on Jun. 4, 2024 and having a size of 18,917 bytes. The information contained in the Sequence Listing is incorporated by reference herein.

TECHNICAL FIELD

The present disclosure generally relates to compositions for regulating the production of fusion proteins. In particular, the present disclosure relates to compositions for regulating gene expression and, consequently, the production of fusion proteins that act as receptors that may be active in the absence of ligands to the receptor.

BACKGROUND

Biological receptors comprise one or more proteins that can cause a change in cellular activity in response to stimuli. The stimuli can be any number of environmental stimuli (internal or external) including, but not limited to, chemical stimuli, thermal stimuli, light stimuli, pressure stimuli, and combinations thereof. Chemical stimuli often come in the form of a molecule, referred to as a ligand, which has a specific shape that enables it to bind with the receptor.

Mu opioid receptors (MOR) can bind a variety of opioid molecules as ligands. MORs are positioned on the surface of pre-synaptic neurons, on post-synaptic cells and within the spinal cord. Binding of an opioid ligand and an MOR may have many physiological effects on a subject, including, but not limited to, feelings of euphoria, sedation and analgesia.

As such, it may be desirable to establish therapies, treatments and/or interventions that may result from having an MOR that may be active in the absence of an opioid ligand.

SUMMARY

Some embodiments of the present disclosure relate to one or more compositions that upregulate the production of one or more sequences of mRNA. The sequences of mRNA may encode for translation of a target biomolecule, thereby causing an increase in bioavailability of the target biomolecule within a subject that is administered the one or more compositions. In some embodiments of the present disclosure, the target biomolecule is a fusion protein with an Fc fragment, such as a mu opioid receptor-Fc (MOR-Fc) that may be biologically active in the absence of an opioid ligand.

In some embodiments of the present disclosure, the compositions comprise a plasmid of deoxyribonucleic acid (DNA) that includes one or more insert sequences of nucleic acids that encode for the production of mRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the mRNA and, consequently, increased translation of the target biomolecule by one or more of the subject's cells.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding an mRNA sequence that encodes for the fusion protein MOR-Fc.

Some embodiments of the present disclosure relate to a method of making a composition/target cell complex. The method comprising a step of administering an RP comprising SEQ ID NO. 1 and SEQ ID NO. 2 to a target cell for forming the composition/target cell complex, wherein the composition/target cell complex causes the target cell to increase production of one or more sequences of mRNA that increases production of a target biomolecule.

Some embodiments of the present disclosure relate to at least one approach for inducing endogenous production of one or more sequences of mRNA that encodes for a target biomolecule, for example MOR-Fc. A first approach utilizes gene vectors containing nucleotide sequences for increasing the endogenous production of one or more sequences of mRNA, which are complete or partial sequences of MOR-Fc and/or combinations thereof, which can be administered to a subject to increase the subject's production of one or more sequences of the mRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred compositions, methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the production by one or more target cells of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a protein-Fc fusion molecule that is found within a subject.

As used therein, the term "target cell" refers to one or more cells and/or cell types that are affected, either directly or indirectly, by a biomolecule.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of mRNA that increases the production of target biomolecules, such as a fusion protein with an Fc fragment. An Fc fragment is the distal portion of the heavy chain of an antibody.

In some embodiments of the present disclosure, the target biomolecule is a mu opioid receptor fused with a Fc (MOR-Fc). In some embodiments of the present disclosure, the MOR-Fc has a physiologic effect that is similar to or substantially the same as a natural MOR that is bound with an opioid ligand.

Some embodiments of the present disclosure relate to a composition that can be administered to a subject with a condition that results, directly or indirectly, from the dysregulated production of a biomolecule. When a therapeutically effective amount of the composition is administered to the subject, the subject may change production and/or functionality of one or more biomolecules.

In some embodiments of the present disclosure, the subject may respond to receiving a therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels of the one or more biomolecules and/or the functionality thereof.

In some embodiments of the present disclosure, administering a therapeutic amount of the composition to a subject upregulates the production, functionality or both of one or more sequences of mRNA that each encode for production of the MOR-Fc biomolecule.

In some embodiments of the present disclosure, the composition is an RP that may be used for gene therapy. The gene therapy is useful for increasing the subject's endogenous production of one or more sequences of mRNA that encode for a target biomolecule. For example, the RP can contain one or more nucleotide sequences that cause increased production of one or more nucleotide sequences that cause an increased production of one or more mRNA sequences that encode for a biomolecule, such as MOR-Fc.

In some embodiments of the present disclosure, the delivery vehicle of the RP used for gene therapy may be a vector that comprises a virus that can be enveloped, or not (un-enveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1\times10^{16}$ TCID$_{50}$/kg (50% tissue culture infective dose per kilogram of the patient's body mass). In some embodiments of the present disclosure, the therapeutically effective amount of the composition that is administered to the patient is about $1\times10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments of the present disclosure, the therapeutically effective amount of the composition is between about 10 and about $1\times10^{16}$ TCP/kg.

Some embodiments of the present disclosure relate to an adeno-associated virus (AAV) genome consisting of an RP that, when operable inside a target cell, will cause the target cell to produce an mRNA sequence that upregulates production of a biomolecule, with an example being MOR-Fc. The RP is comprised of AAV2 inverted terminal repeats (ITRs), a composite CASI promoter, and a human growth hormone (HGH) signal peptide, followed by a mRNA expression cassette encoding for MOR-Fc, followed by a Woodchuck Hepatitis Virus post-transcriptional regulatory element (WPRE) and a Simian virus 40 (SV40) polyadenylation (polyA) signal.

```
SEQ ID NO. 1 (backbone sequence No. 1):
5'

TTCTAGAATAATCAACCTCTGGATTACAAAATTTGTGAAAGATTGACTGGTATTCTT

AACTATGTTGCTCCTTTTACGCTATGTGGATACGCTGCTTTAATGCCTTTGTATCATG

CTATTGCTTCCCGTATGGCTTTCATTTTCTCCTCCTTGTATAAATCCTGGTTGCTGTCT

CTTTATGAGGAGTTGTGGCCCGTTGTCAGGCAACGTGGCGTGGTGTGCACTGTGTTT

GCTGACGCAACCCCCACTGGTTGGGGCATTGCCACCACCTGTCAGCTCCTTTCCGGG

ACTTTCGCTTTCCCCCTCCCTATTGCCACGGCGGAACTCATCGCCGCCTGCCTTGCCC

GCTGCTGGACAGGGGCTCGGCTGTTGGGCACTGACAATTCCGTGGTGTTGTCGGGGA

AATCATCGTCCTTTCCTTGGCTGCTCGCCTGTGTTGCCACCTGGATTCTGCGCGGGAC

GTCCTTCTGCTACGTCCCTTCGGCCCTCAATCCAGCGGACCTTCCTTCCCGCGGCCTG

CTGCCGGCTCTGCGGCCTCTTCCGCGTCTTCGCCTTCGCCCTCAGACGAGTCGGATCT

CCCTTTGGGCCGCCTCCCCGCCTAAGCTTATCGATACCGTCGAGATCTAACTTGTTTA

TTGCAGCTTATAATGGTTACAAATAAAGCAATAGCATCACAAATTTCACAAATAAAG

CATTTTTTTCACTGCATTCTAGTTGTGGTTTGTCCAAACTCATCAATGTATCTTATCAT

GTCTGGATCTCGACCTCGACTAGAGCATGGCTACGTAGATAAGTAGCATGGCGGGTT

AATCATTAACTACAAGGAACCCCTAGTGATGGAGTTGGCCACTCCCTCTCTGCGCGC

TCGCTCGCTCACTGAGGCCGGGCGACCAAAGGTCGCCCGACGCCCGGGCTTTGCCC

GGGCGGCCTCAGTGAGCGAGCGAGCGCGCCAGCTGGCGTAATAGCGAAGAGGCCC

GCACCGATCGCCCTTCCCAACAGTTGCGCAGCCTGAATGGCGAATGGAATTCCAGA

CGATTGAGCGTCAAAATGTAGGTATTTCCATGAGCGTTTTTCCTGTTGCAATGGCTG

GCGGTAATATTGTTCTGGATATTACCAGCAAGGCCGATAGTTTGAGTTCTTCTACTC

AGGCAAGTGATGTTATTACTAATCAAAGAAGTATTGCGACAACGGTTAATTTGCGTG

ATGGACAGACTCTTTTACTCGGTGGCCTCACTGATTATAAAAACACTTCTCAGGATT

CTGGCGTACCGTTCCTGTCTAAAATCCCTTTAATCGGCCTCCTGTTTAGCTCCCGCTC

TGATTCTAACGAGGAAAGCACGTTATACGTGCTCGTCAAAGCAACCATAGTACGCG

CCCTGTAGCGGCGCATTAAGCGCGGCGGGTGTGGTGGTTACGCGCAGCGTGACCGC
```

-continued

```
TACACTTGCCAGCGCCCTAGCGCCCGCTCCTTTCGCTTTCTTCCCTTCCTTTCTCGCC

ACGTTCGCCGGCTTTCCCCGTCAAGCTCTAAATCGGGGGCTCCCTTTAGGGTTCCGA

TTTAGTGCTTTACGGCACCTCGACCCCAAAAAACTTGATTAGGGTGATGGTTCACGT

AGTGGGCCATCGCCCTGATAGACGGTTTTTCGCCCTTTGACGTTGGAGTCCACGTTCT

TTAATAGTGGACTCTTGTTCCAAACTGGAACAACACTCAACCCTATCTCGGTCTATTC

TTTTGATTTATAAGGGATTTTGCCGATTTCGGCCTATTGGTTAAAAAATGAGCTGATT

TAACAAAAATTTAACGCGAATTTTAACAAAATATTAACGTTTACAATTTAAATATTT

GCTTATACAATCTTCCTGTTTTTGGGGCTTTTCTGATTATCAACCGGGGTACATATGA

TTGACATGCTAGTTTTACGATTACCGTTCATCGATTCTCTTGTTTGCTCCAGACTCTC

AGGCAATGACCTGATAGCCTTTGTAGAGACCTCTCAAAAATAGCTACCCTCTCCGGC

ATGAATTTATCAGCTAGAACGGTTGAATATCATATTGATGGTGATTTGACTGTCTCC

GGCCTTTCTCACCCGTTTGAATCTTTACCTACACATTACTCAGGCATTGCATTTAAAA

TATATGAGGGTTCTAAAAATTTTTATCCTTGCGTTGAAATAAAGGCTTCTCCCGCAA

AAGTATTACAGGGTCATAATGTTTTTGGTACAACCGATTTAGCTTTATGCTCTGAGG

CTTTATTGCTTAATTTTGCTAATTCTTTGCCTTGCCTGTATGATTATTGGATGTTGGA

ATTCCTGATGCGGTATTTTCTCCTTACGCATCTGTGCGGTATTTCACACCGCATATGG

TGCACTCTCAGTACAATCTGCTCTGATGCCGCATAGTTAAGCCAGCCCCGACACCCG

CCAACACCCGCTGACGCGCCCTGACGGGCTTGTCTGCTCCCGGCATCCGCTTACAGA

CAAGCTGTGACCGTCTCCGGGAGCTGCATGTGTCAGAGGTTTTCACCGTCATCACCG

AAACGCGCGAGACGAAAGGGCCTCGTGATACGCCTATTTTTATAGGTTAATGTCATG

ATAATAATGGTTTCTTAGACGTCAGGTGGCACTTTTCGGGGAAATGTGCGCGGAACC

CCTATTTGTTTATTTTTCTAAATACATTCAAATATGTATCCGCTCATGAGACAATAAC

CCTGATAAATGCTTCAATAATATTGAAAAAGGAAGAGTATGAGTATTCAACATTTCC

GTGTCGCCCTTATTCCCTTTTTTGCGGCATTTTGCCTTCCTGTTTTTGCTCACCCAGAA

ACGCTGGTGAAAGTAAAAGATGCTGAAGATCAGTTGGGTGCACGAGTGGGTTACAT

CGAACTGGATCTCAACAGCGGTAAGATCCTTGAGAGTTTTCGCCCCGAAGAACGTTT

TCCAATGATGAGCACTTTTAAAGTTCTGCTATGTGGCGCGGTATTATCCCGTATTGAC

GCCGGGCAAGAGCAACTCGGTCGCCGCATACACTATTCTCAGAATGACTTGGTTGAG

TACTCACCAGTCACAGAAAAGCATCTTACGGATGGCATGACAGTAAGAGAATTATG

CAGTGCTGCCATAACCATGAGTGATAACACTGCGGCCAACTTACTTCTGACAACGAT

CGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACT

ACTTACTCTAGCTTCCCGGCAACAATTAATAGACTGGATGGAGGCGGATAAAGTTGC

AGGACCACTTCTGCGCTCGGCCCTTCCGGCTGGCTGGTTTATTGCTGATAAATCTGG

AGCCGGTGAGCGTGGGTCTCGCGGTATCATTGCAGCACTGGGGCCAGATGGTAAGC

CCTCCCGTATCGTAGTTATCTACACGACGGGGAGTCAGGCAACTATGGATGAACGA

AATAGACAGATCGCTGAGATAGGTGCCTCACTGATTAAGCATTGGTAACTGTCAGAC

CAAGTTTACTCATATATACTTTAGATTGATTTAAAACTTCATTTTTAATTTAAAAGGA

TCTAGGTGAAGATCCTTTTTGATAATCTCATGACCAAAATCCCTTAACGTGAGTTTTC

GTTCCACTGAGCGTCAGACCCCGTAGAAAAGATCAAAGGATCTTCTTGAGATCCTTT
```

-continued

TTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAG

AGCGCAGATACCAAATACTGTCCTTCTAGTGTAGCCGTAGTTAGGCCACCACTTCAA

GAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGA

TAAGGCGCAGCGGTCGGGCTGAACGGGGGGTTCGTGCACACAGCCCAGCTTGGAGC

GAACGACCTACACCGAACTGAGATACCTACAGCGTGAGCTATGAGAAAGCGCCACG

CTTCCCGAAGGGAGAAAGGCGGACAGGTATCCGGTAAGCGGCAGGGTCGGAACAG

GAGAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGGCGG

AGCCTATGGAAAAACGCCAGCAACGCGGCCTTTTTACGGTTCCTGGCCTTTTGCTGG

CCTTTTGCTCACATGTTCTTTCCTGCGTTATCCCCTGATTCTGTGGATAACCGTATTAC

CGCCTTTGAGTGAGCTGATACCGCTCGCCGCAGCCGAACGACCGAGCGCAGCGAGT

CAGTGAGCGAGGAAGCGGAAGAGCGCCCAATACGCAAACCGCCTCTCCCCGCGCGT

TGGCCGATTCATTAATGCAGCAGCTGCGCGCTCGCTCGCTCACTGAGGCCGCCCGGG

CAAAGCCCGGGCGTCGGGCGACCTTTGGTCGCCCGGCCTCAGTGAGCGAGCGAGCG

CGCAGAGAGGGAGTGGCCAACTCCATCACTAGGGGTTCCTTGTAGTTAATGATTAAC

CCGCCATGCTACTTATCTACGTAGCCATGCTCTAGGACATTGATTATTGACTAGTGG

AGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTT

TCCATTGACGTCAATGGGTGGAGTATTTACGGTAAACTGCCCACTTGGCAGTACATC

AAGTGTATCATATGCCAAGTACGCCCCCTATTGACGTCAATGACGGTAAATGGCCCG

CCTGGCATTATGCCCAGTACATGACCTTATGGGACTTTCCTACTTGGCAGTACATCTA

CGTATTAGTCATCGCTATTACCATGGTCGAGGTGAGCCCCACGTTCTGCTTCACTCTC

CCCATCTCCCCCCCCTCCCCACCCCCAATTTTGTATTTATTTATTTTTTAATTATTTTG

TGCAGCGATGGGGGGGGGGGGGGGGGCGCGCGCCAGGCGGGGGGGCGGG

GCGAGGGGCGGGCGGGGCGAGGCGGAGAGGTGCGGCGGCAGCCAATCAGAGCGG

CGCGCTCCGAAAGTTTCCTTTTATGGCGAGGCGGCGGCGGCGGCGGCCCTATAAAA

AGCGAAGCGCGCGGCGGGCGGGAGTCGCTGCGCGCTGCCTTCGCCCCGTGCCCCGC

TCCGCCGCCGCCTCGCGCCGCCCGCCCCGGCTCTGACTGACCGCGTTACTAAAACAG

GTAAGTCCGGCCTCCGCGCCGGGTTTTGGCGCCTCCCGCGGGCGCCCCCCTCCTCAC

GGCGAGCGCTGCCACGTCAGACGAAGGGCGCAGCGAGCGTCCTGATCCTTCCGCCC

GGACGCTCAGGACAGCGGCCCGCTGCTCATAAGACTCGGCCTTAGAACCCCAGTAT

CAGCAGAAGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGCGGAGGG

-continued

```
ATCTCCGTGGGGCGGTGAACGCCGATGATGCCTCTACTAACCATGTTCATGTTTTCTT

TTTTTTTCTACAGGTCCTGGGTGACGAACAGGGTACCGCCACCATGAGGGGCATGAA

GCTGCTGGGGCGCTGCTGGCACTGGCGGCCCTACTGCAGGGGCCGTGTCC
```

3'

SEQ ID NO. 2 (mRNA expression cassette No. 2 - MOR-Fc):
5'

```
ATGGATAGCAGCGCGGCGCCGACCAACGCGAGCAACTGCACCGATGCGCTGGCGTA

TAGCAGCTGCAGCCCGGCGCCGAGCCCGGGCAGCTGGGTGAACCTGAGCCATCTGG

ATGGCAACCTGAGCGATCCGTGCGGCCCGAACCGCACCGATCTGGGCGGCCGCGAT

AGCCTGTGCCCGCCGACCGGCAGCCCGAGCATGATTACCGCGATTACCATTATGGCG

CTGTATAGCATTGTGTGCGTGGTGGGCCTGTTTGGCAACTTTCTGGTGATGTATGTGA

TTGTGCGCTATACCAAAATGAAAACCGCGACCAACATTTATATTTTTAACCTGGCGC

TGGCGGATGCGCTGGCGACCAGCACCCTGCCGTTTCAGAGCGTGAACTATCTGATGG

GCACCTGGCCGTTTGGCACCATTCTGTGCAAAATTGTGATTAGCATTGATTATTATA

ACATGTTTACCAGCATTTTTACCCTGTGCACCATGAGCGTGGATCGCTATATTGCGGT

GTGCCATCCGGTGAAAGCGCTGGATTTTCGCACCCCGCGCAACGCGAAAATTATTAA

CGTGTGCAACTGGATTCTGAGCAGCGCGATTGGCCTGCCGGTGATGTTTATGGCGAC

CACCAAATATCGCCAGGGCAGCATTGATTGCACCCTGACCTTTAGCCATCCGACCTG

GTATTGGGAAAACCTGCTGAAAATTTGCGTGTTTATTTTTGCGTTTATTATGCCGGTG

CTGATTATTACCGTGTGCTATGGCCTGATGATTCTGCGCCTGAAAAGCGTGCGCATG

CTGAGCGGCAGCAAAGAAAAAGATCGCAACCTGCGCAAAATTACCCGCATGGTGCT

GGTGGTGGTGGCGGTGTTTATTGTGTGCTGGACCCCGATTCATATTTATGTGATTATT

AAAGCGCTGGTGACCATTCCGGAAACCACCTTTCAGACCGTGAGCTGGCATTTTTGC

ATTGCGCTGGGCTATACCAACAGCTGCCTGAACCCGGTGCTGTATGCGTTTCTGGAT

GAAAACTTTAAACGCTGCTTTCGCGAATTTTGCATTCCGACCAGCAGCAACATTGAA

CAGCAGAACAGCACCCGCATTCGCCAGAACACCCGCGATCATCCGAGCACCGCGAA

CACCGTGGATCGCACCAACCATCAGCTGGAAAACCTGGAAGCGGAAACCGCGCCGC

TGCCGGGGCGGATCAGGCGGATCACCCAAATCTTGTGACAAAACTCACACATGCCC

ACCGTGCCCAGCACCTGAACTCCTGGGGGGACCGTCAGTCTTCCTCTTCCCCCCAAA

ACCCAAGGACACCCTCATGATCTCCCGGACCCCTGAGGTCACATGCGTGGTGGTGG

ACGTGAGCCACGAAGACCCTGAGGTCAAGTTCAACTGGTACGTGGACGGCGTGGAG

GTGCATAATGCCAAGACAAAGCCGCGGGAGGAGCAGTACAACAGCACGTACCGTGT

GGTCAGCGTCCTCACCGTCCTGCACCAGGACTGGCTGAATGGCAAGGAGTACAAGT

GCAAGGTCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGAGGAGAT

GACCAAGAACCAGGTCAGCCTGACCTGCCTGGTCAAAGGCTTCTATCCCAGCGACA

TCGCCGTGGAGTGGGAGAGCAATGGGCAGCCGGAGAACAACTACAAGACCACGCCT

CCCGTGCTGGACTCCGACGGCTCCTTCTTCCTCTACAGCAAGCTCACCGTGGACAAG

AGCAGGTGGCAGCAGGGGAACGTCTTCTCATGCTCCGTGATGCATGAGGCTCTGCAC

AACCACTACACGCAGAAGAGCCTCTCCCTGTCTCCGGGTAAATAG
```

3'

-continued

SEQ ID NO. 3 = SEQ ID NO. 1 + SEQ ID NO. 2
5'

TTCTAGAATAATCAACCTCTGGATTACAAAATTTGTGAAAGATTGACTGGTATTCTT

AACTATGTTGCTCCTTTTACGCTATGTGGATACGCTGCTTTAATGCCTTTGTATCATG

CTATTGCTTCCCGTATGGCTTTCATTTTCTCCTCCTTGTATAAATCCTGGTTGCTGTCT

CTTTATGAGGAGTTGTGGCCCGTTGTCAGGCAACGTGGCGTGGTGTGCACTGTGTTT

GCTGACGCAACCCCCACTGGTTGGGGCATTGCCACCACCTGTCAGCTCCTTTCCGGG

ACTTTCGCTTTCCCCCTCCCTATTGCCACGGCGGAACTCATCGCCGCCTGCCTTGCCC

GCTGCTGGACAGGGGCTCGGCTGTTGGGCACTGACAATTCCGTGGTGTTGTCGGGGA

AATCATCGTCCTTTCCTTGGCTGCTCGCCTGTGTTGCCACCTGGATTCTGCGCGGGAC

GTCCTTCTGCTACGTCCCTTCGGCCCTCAATCCAGCGGACCTTCCTTCCCGCGGCCTG

CTGCCGGCTCTGCGGCCTCTTCCGCGTCTTCGCCTTCGCCCTCAGACGAGTCGGATCT

CCCTTTGGGCCGCCTCCCCGCCTAAGCTTATCGATACCGTCGAGATCTAACTTGTTTA

TTGCAGCTTATAATGGTTACAAATAAAGCAATAGCATCACAAATTTCACAAATAAAG

CATTTTTTTCACTGCATTCTAGTTGTGGTTTGTCCAAACTCATCAATGTATCTTATCAT

GTCTGGATCTCGACCTCGACTAGAGCATGGCTACGTAGATAAGTAGCATGGCGGGTT

AATCATTAACTACAAGGAACCCCTAGTGATGGAGTTGGCCACTCCCTCTCTGCGCGC

TCGCTCGCTCACTGAGGCCGGGCGACCAAAGGTCGCCCGACGCCCGGGCTTTGCCC

GGGCGGCCTCAGTGAGCGAGCGAGCGCGCCAGCTGGCGTAATAGCGAAGAGGCCC

GCACCGATCGCCCTTCCCAACAGTTGCGCAGCCTGAATGGCGAATGGAATTCCAGA

CGATTGAGCGTCAAAATGTAGGTATTTCCATGAGCGTTTTTCCTGTTGCAATGGCTG

GCGGTAATATTGTTCTGGATATTACCAGCAAGGCCGATAGTTTGAGTTCTTCTACTC

AGGCAAGTGATGTTATTACTAATCAAAGAAGTATTGCGACAACGGTTAATTTGCGTG

ATGGACAGACTCTTTTACTCGGTGGCCTCACTGATTATAAAAACACTTCTCAGGATT

CTGGCGTACCGTTCCTGTCTAAAATCCCTTTAATCGGCCTCCTGTTTAGCTCCCGCTC

TGATTCTAACGAGGAAAGCACGTTATACGTGCTCGTCAAAGCAACCATAGTACGCG

CCCTGTAGCGGCGCATTAAGCGCGGCGGGTGTGGTGGTTACGCGCAGCGTGACCGC

TACACTTGCCAGCGCCCTAGCGCCCGCTCCTTTCGCTTTCTTCCCTTCCTTTCTCGCC

ACGTTCGCCGGCTTTCCCCGTCAAGCTCTAAATCGGGGGCTCCCTTTAGGGTTCCGA

TTTAGTGCTTTACGGCACCTCGACCCCAAAAAACTTGATTAGGGTGATGGTTCACGT

AGTGGGCCATCGCCCTGATAGACGGTTTTTCGCCCTTTGACGTTGGAGTCCACGTTCT

TTAATAGTGGACTCTTGTTCCAAACTGGAACAACACTCAACCCTATCTCGGTCTATTC

TTTTGATTTATAAGGGATTTTGCCGATTTCGGCCTATTGGTTAAAAAATGAGCTGATT

TAACAAAAATTTAACGCGAATTTTAACAAAATATTAACGTTTACAATTTAAATATTT

GCTTATACAATCTTCCTGTTTTTGGGGCTTTTCTGATTATCAACCGGGGTACATATGA

TTGACATGCTAGTTTTACGATTACCGTTCATCGATTCTCTTGTTTGCTCCAGACTCTC

AGGCAATGACCTGATAGCCTTTGTAGAGACCTCTCAAAAATAGCTACCCTCTCCGGC

ATGAATTTATCAGCTAGAACGGTTGAATATCATATTGATGGTGATTTGACTGTCTCC

GGCCTTTCTCACCCGTTTGAATCTTTACCTACACATTACTCAGGCATTGCATTTAAAA

TATATGAGGGTTCTAAAAATTTTTATCCTTGCGTTGAAATAAAGGCTTCTCCCGCAA

AAGTATTACAGGGTCATAATGTTTTTGGTACAACCGATTTAGCTTTATGCTCTGAGG

-continued

```
CTTTATTGCTTAATTTTGCTAATTCTTTGCCTTGCCTGTATGATTTATTGGATGTTGGA

ATTCCTGATGCGGTATTTTCTCCTTACGCATCTGTGCGGTATTTCACACCGCATATGG

TGCACTCTCAGTACAATCTGCTCTGATGCCGCATAGTTAAGCCAGCCCCGACACCCG

CCAACACCCGCTGACGCGCCCTGACGGGCTTGTCTGCTCCCGGCATCCGCTTACAGA

CAAGCTGTGACCGTCTCCGGGAGCTGCATGTGTCAGAGGTTTTCACCGTCATCACCG

AAACGCGCGAGACGAAAGGGCCTCGTGATACGCCTATTTTTATAGGTTAATGTCATG

ATAATAATGGTTTCTTAGACGTCAGGTGGCACTTTTCGGGGAAATGTGCGCGGAACC

CCTATTTGTTTATTTTTCTAAATACATTCAAATATGTATCCGCTCATGAGACAATAAC

CCTGATAAATGCTTCAATAATATTGAAAAAGGAAGAGTATGAGTATTCAACATTTCC

GTGTCGCCCTTATTCCCTTTTTTGCGGCATTTTGCCTTCCTGTTTTTGCTCACCCAGAA

ACGCTGGTGAAAGTAAAAGATGCTGAAGATCAGTTGGGTGCACGAGTGGGTTACAT

CGAACTGGATCTCAACAGCGGTAAGATCCTTGAGAGTTTTCGCCCCGAAGAACGTTT

TCCAATGATGAGCACTTTTAAAGTTCTGCTATGTGGCGCGGTATTATCCCGTATTGAC

GCCGGGCAAGAGCAACTCGGTCGCCGCATACACTATTCTCAGAATGACTTGGTTGAG

TACTCACCAGTCACAGAAAAGCATCTTACGGATGGCATGACAGTAAGAGAATTATG

CAGTGCTGCCATAACCATGAGTGATAACACTGCGGCCAACTTACTTCTGACAACGAT

CGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACT

ACTTACTCTAGCTTCCCGGCAACAATTAATAGACTGGATGGAGGCGGATAAAGTTGC

AGGACCACTTCTGCGCTCGGCCCTTCCGGCTGGCTGGTTTATTGCTGATAAATCTGG

AGCCGGTGAGCGTGGGTCTCGCGGTATCATTGCAGCACTGGGGCCAGATGGTAAGC

CCTCCCGTATCGTAGTTATCTACACGACGGGGAGTCAGGCAACTATGGATGAACGA

AATAGACAGATCGCTGAGATAGGTGCCTCACTGATTAAGCATTGGTAACTGTCAGAC

CAAGTTTACTCATATATACTTTAGATTGATTTAAAACTTCATTTTTAATTTAAAAGGA

TCTAGGTGAAGATCCTTTTTGATAATCTCATGACCAAAATCCCTTAACGTGAGTTTTC

GTTCCACTGAGCGTCAGACCCCGTAGAAAAGATCAAAGGATCTTCTTGAGATCCTTT

TTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAG

AGCGCAGATACCAAATACTGTCCTTCTAGTGTAGCCGTAGTTAGGCCACCACTTCAA

GAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGA

TAAGGCGCAGCGGTCGGGCTGAACGGGGGGTTCGTGCACACAGCCCAGCTTGGAGC

GAACGACCTACACCGAACTGAGATACCTACAGCGTGAGCTATGAGAAAGCGCCACG

CTTCCCGAAGGGAGAAAGGCGGACAGGTATCCGGTAAGCGGCAGGGTCGGAACAG

GAGAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGCGG

AGCCTATGGAAAAACGCCAGCAACGCGGCCTTTTTACGGTTCCTGGCCTTTTGCTGG

CCTTTTGCTCACATGTTCTTTCCTGCGTTATCCCCTGATTCTGTGGATAACCGTATTAC

CGCCTTTGAGTGAGCTGATACCGCTCGCCGCAGCCGAACGACCGAGCGCAGCGAGT

CAGTGAGCGAGGAAGCGGAAGAGCGCCCAATACGCAAACCGCCTCTCCCCGCGCGT
```

-continued

```
TGGCCGATTCATTAATGCAGCAGCTGCGCGCTCGCTCGCTCACTGAGGCCGCCCGGG

CAAAGCCCGGGCGTCGGGCGACCTTTGGTCGCCCGGCCTCAGTGAGCGAGCGAGCG

CGCAGAGAGGGAGTGGCCAACTCCATCACTAGGGGTTCCTTGTAGTTAATGATTAAC

CCGCCATGCTACTTATCTACGTAGCCATGCTCTAGGACATTGATTATTGACTAGTGG

AGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTT

TCCATTGACGTCAATGGGTGGAGTATTTACGGTAAACTGCCCACTTGGCAGTACATC

AAGTGTATCATATGCCAAGTACGCCCCCTATTGACGTCAATGACGGTAAATGGCCCG

CCTGGCATTATGCCCAGTACATGACCTTATGGGACTTTCCTACTTGGCAGTACATCTA

CGTATTAGTCATCGCTATTACCATGGTCGAGGTGAGCCCCACGTTCTGCTTCACTCTC

CCCATCTCCCCCCCCTCCCCACCCCCAATTTTGTATTTATTTATTTTTTAATTATTTTG

TGCAGCGATGGGGGCGGGGGGGGGGGGGGCGCGCGCCAGGCGGGGGGGGCGGG

GCGAGGGGCGGGGCGGGGCGAGGCGGAGAGGTGCGGCGGCAGCCAATCAGAGCGG

CGCGCTCCGAAAGTTTCCTTTTATGGCGAGGCGGCGGCGGCGGCCCTATAAAA

AGCGAAGCGCGCGGCGGGCGGGAGTCGCTGCGCGCTGCCTTCGCCCCGTGCCCCGC

TCCGCCGCCGCCTCGCGCCGCCCGCCCCGGCTCTGACTGACCGCGTTACTAAAACAG

GTAAGTCCGGCCTCCGCGCCGGGTTTTGGCGCCTCCCGCGGGCGCCCCCCTCCTCAC

GGCGAGCGCTGCCACGTCAGACGAAGGGCGCAGCGAGCGTCCTGATCCTTCCGCCC

GGACGCTCAGGACAGCGGCCCGCTGCTCATAAGACTCGGCCTTAGAACCCCAGTAT

CAGCAGAAGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGCGGAGGG

ATCTCCGTGGGCGGTGAACGCCGATGATGCCTCTACTAACCATGTTCATGTTTTCTT

TTTTTTTCTACAGGTCCTGGGTGACGAACAGGGTACCGCCACCATGAGGGGCATGAA

GCTGCTGGGGCGCTGCTGGCACTGGCGGCCCTACTGCAGGGGGCCGTGTCC

ATGGATAGCAGCGCGGCGCCGACCAACGCGAGCAACTGCACCGATGCGCTGGCGTA

TAGCAGCTGCAGCCCGGCGCCGAGCCCGGGCAGCTGGGTGAACCTGAGCCATCTGG

ATGGCAACCTGAGCGATCCGTGCGGCCCGAACCGCACCGATCTGGGCGGCCGCGAT

AGCCTGTGCCCGCCGACCGGCAGCCCGAGCATGATTACCGCGATTACCATTATGGCG

CTGTATAGCATTGTGTGCGTGGTGGGCCTGTTTGGCAACTTTCTGGTGATGTATGTGA

TTGTGCGCTATACCAAAATGAAAACCGCGACCAACATTTATATTTTTAACCTGGCGC

TGGCGGATGCGCTGGCGACCAGCACCCTGCCGTTTCAGAGCGTGAACTATCTGATGG

GCACCTGGCCGTTTGGCACCATTCTGTGCAAAATTGTGATTAGCATTGATTATTATA

ACATGTTTACCAGCATTTTTACCCTGTGCACCATGAGCGTGGATCGCTATATTGCGGT

GTGCCATCCGGTGAAAGCGCTGGATTTTCGCACCCCGCGCAACGCGAAAATTATTAA

CGTGTGCAACTGGATTCTGAGCAGCGCGATTGGCCTGCCGGTGATGTTTATGGCGAC

CACCAAATATCGCCAGGGCAGCATTGATTGCACCCTGACCTTTAGCCATCCGACCTG

GTATTGGGAAAACCTGCTGAAAATTTGCGTGTTTATTTTTGCGTTTATTATGCCGGTG

CTGATTATTACCGTGTGCTATGGCCTGATGATTCTGCGCCTGAAAAGCGTGCGCATG

CTGAGCGGCAGCAAAGAAAAAGATCGCAACCTGCGCAAAATTACCCGCATGGTGCT

GGTGGTGGTGGCGGTGTTTATTGTGTGCTGGACCCCGATTCATATTTATGTGATTATT
```

-continued

```
AAAGCGCTGGTGACCATTCCGGAAACCACCTTTCAGACCGTGAGCTGGCATTTTTGC

ATTGCGCTGGGCTATACCAACAGCTGCCTGAACCCGGTGCTGTATGCGTTTCTGGAT

GAAAACTTTAAACGCTGCTTTCGCGAATTTTGCATTCCGACCAGCAGCAACATTGAA

CAGCAGAACAGCACCCGCATTCGCCAGAACACCCGCGATCATCCGAGCACCGCGAA

CACCGTGGATCGCACCAACCATCAGCTGGAAAACCTGGAAGCGGAAACCGCGCCGC

TGCCGGGGCGGATCAGGCGGATCACCCAAATCTTGTGACAAAACTCACACATGCCC

ACCGTGCCCAGCACCTGAACTCCTGGGGGGACCGTCAGTCTTCCTCTTCCCCCCAAA

ACCCAAGGACACCCTCATGATCTCCCGGACCCCTGAGGTCACATGCGTGGTGGTGG

ACGTGAGCCACGAAGACCCTGAGGTCAAGTTCAACTGGTACGTGGACGGCGTGGAG

GTGCATAATGCCAAGACAAAGCCGCGGGAGGAGCAGTACAACAGCACGTACCGTGT

GGTCAGCGTCCTCACCGTCCTGCACCAGGACTGGCTGAATGGCAAGGAGTACAAGT

GCAAGGTCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGAGGAGAT

GACCAAGAACCAGGTCAGCCTGACCTGCCTGGTCAAAGGCTTCTATCCCAGCGACA

TCGCCGTGGAGTGGGAGAGCAATGGGCAGCCGGAGAACAACTACAAGACCACGCCT

CCCGTGCTGGACTCCGACGGCTCCTTCTTCCTCTACAGCAAGCTCACCGTGGACAAG

AGCAGGTGGCAGCAGGGGAACGTCTTCTCATGCTCCGTGATGCATGAGGCTCTGCAC

AACCACTACACGCAGAAGAGCCTCTCCCTGTCTCCGGGTAAATAG

3'
```

As will be appreciated by those skilled in the art, because the recombinant plasmid is a circular vector, the one or more sequences of the mRNA expression cassettes may be connected at the 3' end of SEQ ID NO. 1, as shown in SEQ ID NO. 3, or at the 5' end of SEQ ID NO. 1.

As will be appreciated by those skilled in the art, a perfect match of nucleotides with each of the nucleotide sequences above is not necessary in order to have the desired result of increased bioavailability of the target biomolecule, MOR-Fc. In some embodiments of the present disclosure, about 80% to about 100% nucleotide sequence matching with each of the mRNA expression cassettes causes the desired result. In some embodiments of the present disclosure, about 85% to about 100% nucleotide sequence matching with each of the mRNA expression cassettes causes the desired result. In some embodiments of the present disclosure, about 90% to about 100% nucleotide sequence matching with each of the mRNA expression cassettes causes the desired result. In some embodiments of the present disclosure, about 95% to about 100% nucleotide sequence matching with each of the mRNA expression cassettes causes the desired result.

Without being bound by any particular theory, the increased bioavailability of MOR-Fc, may allow for the subject to experience some or further physiologic effects as if there was an opioid ligand present in their bloodstream, when there may be little or no such opioid present. As such, a subject whose has increased bioavailability of the MOR-Fc, may experience euphoria, sedation and analgesia, whereas they would not experience these feelings without the increased bioavailability of the MOR-Fc or without the presence of opioid ligands in their bloodstream.

Example 1—Expression Cassette

Expression cassettes for expressing mRNA were synthesized. The synthesized mRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mRNA expression cassette was amplified by polymerase chain reaction (PCR) using Taq polymerase and the PCR products were gel purified. The bands of interest were also excised and purified using a gel extraction kit. These PCR products contained the mRNA expression cassettes in addition to 15 base pair 5' and 3' overhangs that aligned with the ends of the linearized pAVA-00200 backbone. Using in-fusion cloning, the amplified mRNA expression cassettes are integrated with the pAVA-00200 backbone via homologous recombination. The resulting RP contained the following: 5' ITR, CASI promoter, mRNA expression cassette, WPRE, SV40 polyA and ITR 3'.

The invention claimed is:

1. A composition that comprises a recombinant plasmid (RP) with a sequence of nucleotides that encodes for a sequence of messenger ribonucleic acid (mRNA) that encodes for a fusion protein consisting of a protein and an Fc fragment, wherein the sequence of nucleotides is about 95% to about 100% identical to SEQ ID NO. 2.

2. The composition of claim 1, wherein the RP is configured to be delivered to a target cell.

3. The composition of claim 1, wherein the RP is encased in a viral vector.

4. The composition of claim 2, wherein the viral vector is one of a double stranded DNA virus, a single stranded DNA virus, a single stranded RNA virus, or a double stranded RNA virus.

5. The composition of claim 3, wherein the viral vector is an adeno-associated virus (AAV).

6. The composition of claim 1, wherein the RP is encased in a protein coat, a lipid vesicle, or any combination thereof.

7. A composition that comprises a RP with a nucleotide sequence encoding a mRNA that encodes a fusion protein consisting of a protein and an Fc fragment wherein the nucleotide sequence is about 95% to about 100% identical to the nucleotide sequence of SEQ ID NO. 3.

* * * * *

SEQUENCE LISTING

```
Sequence total quantity: 3
SEQ ID NO: 1            moltype = DNA  length = 5927
FEATURE                 Location/Qualifiers
```

```
source                  1..5927
                        mol_type = other DNA
                        organism = synthetic construct
SEQUENCE: 1
ttctagaata atcaacctct ggattacaaa atttgtgaaa gattgactgg tattcttaac    60
tatgttgctc cttttacgct atgtggatac gctgctttaa tgcctttgta tcatgctatt   120
gcttcccgta tggctttcat tttctcctcc ttgtataaat cctggttgct gtctctttat   180
gaggagttgt ggcccgttgt caggcaacgt ggcgtggtgt gcactgtgtt tgctgacgca   240
accccactg gttgggcat tgccaccacc tgtcagctcc tttccgggac tttcgctttc     300
cccctcccta ttgccacggc ggaactcatc gccgcctgcc ttgcccgctg ctggacaggg   360
gctcggctgt tgggcactga caattccgtg tgttgtcgg ggaaatcatc gtcctttcct    420
tggctgctcg cctgtgttgc cacctggatt ctgcgcggga cgtccttctg ctacgtccct   480
tcggccctca atccagcgga ccttcctccc cgcggcctgc tgccggctct gcggcctctt   540
ccgcgtcttc gccttcgccc tcagacgagt cggatctccc tttgggccgc ctccccgcct   600
aagcttatcg ataccgtcga gatctaactt gtttattgca gcttataatg gttacaaata   660
aagcaatagc atcacaaatt tcacaaataa agcatttttt tcactgcatt ctagttgtgg   720
tttgtccaaa ctcatcaatg tatcttatca tgtctggatc tcgacctcga ctagagcatg   780
gctacgtaga taagtagcat ggcgggttaa tcattaacta caaggaaccc ctagtgatgg   840
agttggccac tccctctctg cgcgctcgct cgctcactga ggccgggcga ccaaaggtcg   900
cccgacgccc gggctttgcc cgggcggcct cagtgagcga gcgagcgcgc cagctggcgt   960
aatagcgaag aggcccgcac cgatcgccct tcccaacagt tgcgcagcct gaatggcgaa  1020
tggaattcca gacgattgag cgtcaaaatg taggtatttc catgagcgtt tttcctgttg  1080
caatggctgg cggtaatatt gttctggata ttaccagcaa ggccgatagt ttgagttctt  1140
ctactcaggc aagtgatgtt attactaatc aaagaagtat tgcgacaacg gttaatttgc  1200
gtgatggaca gactctttta ctcggtggcc tcactgatta taaaaacact tctcaggatt  1260
ctggcgtacc gttcctgtct aaaatccctt taatgcggtc cctgtttagt tcccgctctg  1320
attctaacga ggaaagcacg ttatacgtgc tcgtcaaagc aaccatagta cgcgccctgt  1380
agcggcgcat taagcgcggc gggtgtggtg gttacgcgca gcgtgaccgc tacacttgcc  1440
agcgccctag cgcccgctcc tttcgctttc ttccctttcct ttctcgccac gttcgccggc  1500
tttcccgtc aagctctaaa tcgggggctc cctttagggg tccgatttag tgctttacgg   1560
cacctcgacc ccaaaaaact tgattaggt gatggttcac gtagtgggcc atcgccctga   1620
tagacggttt ttcgcccttt gacgttggag tccacgttct ttaatagtgg actcttgttc   1680
caaactggaa caacactcaa ccctatctcg gtctattctt ttgatttata agggatttg    1740
ccgatttcgg cctattggtt aaaaaatgag ctgatttaac aaaaatttaa cgcgaattt    1800
aacaaaatat taacgttac aatttaaata tttgcttata caatcttcct gttttggggc    1860
cttttctgat tatcaaccgg ggtacatatg attgacatgc tagttttacg attaccgttc   1920
atcgattctc ttgtttgctc cagactctca ggcaatgacc tgatagcctt tgtagagacc   1980
tctcaaaaat agctaccctc tccggcatga atttatcagc tagaacggtt gaatatcata   2040
ttgatggtga tttgactgtc tccggccttt ctcacccgtt tgaatcttta cctacacatt   2100
actcaggcat tgcatttaaa atatatgagg gttctaaaaa tttttatcct tgcgttgaaa   2160
taaaggcttc tcccgcaaaa gtattacagg tcataatgt ttttggtaca accgatttag    2220
ctttatgctc tgaggcttta ttgcttaatt tgctaattc tttgccttgc ctgtatgatt    2280
tattgatgt tggaattcct gatgcggtat tttctcctta cgcatctgtg cggtatttca    2340
caccgcatat ggtgcactct cagtacaatc tgctctgatg ccgcatagtt aagccagccc   2400
cgacacccgc caacccgc tgacgcgccc tgacgggctt gtctgctccc ggcatccgct      2460
tacagacaag ctgtgaccgt ctccgggagc tgcatgtgtc agaggttttc accgtcatca   2520
ccgaaacgcg cgagacgaaa gggcctcgtg atacgcctat ttttataggt taatgtcatg   2580
ataataatgg tttcttagac gtcaggtggc acttttcggg gaaatgtgcg cggaaccccc   2640
atttgtttat ttttctaaat acattcaaat atgtatccgc tcatgagaca ataaccctga   2700
taaatgcttc aataatattg aaaaaggaag agtatgagta ttcaacattt ccgtgtcgcc   2760
cttattccct tttttgcggc atttttgcctt cctgttttt ctcacccaga aacgctggtg    2820
aaagtaaaag atgctgaaga tcagttgggt gcacgagtgg gttacatcga actggatctc   2880
aacagcggta agatcttga gagttttcgc cccgaagaac gttttccaat gatgagcact    2940
tttaaagttc tgctatgtgg cgcggtatta tcccgtattg acgccgggca agagcaactc   3000
ggtcgccgca tacactattc tcagaatgac ttggttgagt actcaccagt acagaaaag    3060
catcttacgg atggcatgac agtaagagaa ttatgcagtg ctgccataac catgagtgat   3120
aacactgcgg ccaacttact tctgacaacg atcggaggac cgaaggagct aaccgctttt   3180
ttgcacaaca tgggggatca tgtaactcgc cttgatcgtt gggaaccgga gctgaatgaa   3240
gccataccaa acgacgagcg tgacaccacg atgcctgtag caatggcaac aacgttgcgc   3300
aaactattaa ctggcgaact acttactcta gcttcccggc aacaattaat agactggatg   3360
gaggcggata aagttgcagg accacttctg cgctcggccc ttccggctgg ctggtttatt   3420
gctgataaat ctggagccgg tgagcgtggg tctcgcggta tcattgcagc actggggcca   3480
gatggtaagc cctcccgtat cgtagttatc tacacgacgg ggagtcaggc aactatggat   3540
gaacgaaata gacagatcgc tgagataggt gcctcactga ttaagcattg gtaactgtca   3600
gaccaagttt actcatatat actttagatt gatttaaaac ttcattttta atttaaaagg   3660
atctaggtga agatcctttt tgataatctc atgaccaaaa tcccttaacg tgagttttcg   3720
ttccactgag cgtcagaccc cgtagaaaag atcaaaggat cttcttgaga tcctttttt    3780
ctgcgcgtaa tctgctgctt gcaaacaaaa aaccaccgc taccagcggt ggtttgtttg    3840
ccggatcaag agctaccaac tctttttccg aaggtaactg gcttcagcag agcgcagata   3900
ccaaatactg tccttctagt gtagccgtag ttaggccacc acttcaagaa ctctgtagca   3960
ccgcctacat acctcgctct gctaatcctg ttaccagtgg ctgctgccag tggcgataag   4020
tcgtgtctta ccgggttgga ctcaagacga tagttaccgg ataaggcgca gcggtcgggc   4080
tgaacggggg gttcgtgcac acagcccagc ttggagcgaa cgacctacac cgaactgaga   4140
tacctacagc gtgagctatg agaaagcgcc acgcttcccg aagggagaaa ggcggacagg   4200
tatccggtaa gcggcagggt cggaacagga gagcgcacga gggagcttcc agggggaaac   4260
gcctggtatc tttatagtcc tgtcgggttt cgccacctct gacttgagcg tcgatttttg   4320
tgatgctcgt caggggggcg gagcctatgg aaaaacgcca gcaacgcggc ctttttacgg   4380
ttcctggcct tttgctggcc ttttgctcac atgttctttc ctgcgttatc ccctgattct   4440
gtggataacc gtattaccgc ctttgagtga gctgataccg ctcgccgcag ccgaacgacc  4500
```

```
gagcgcagcg agtcagtgag cgaggaagcg gaagagcgcc caatacgcaa accgcctctc 4560
cccgcgcgtt ggccgattca ttaatgcagc agctgcgcgc tcgctcgctc actgaggccg 4620
cccgggcaaa gcccgggcgt cgggcgacct ttggtcgccc ggcctcagtg agcgagcgag 4680
cgcgcagaga gggagtggcc aactccatca ctaggggttc cttgtagtta atgattaacc 4740
cgccatgcta cttatctacg tagccatgct ctaggacatt gattattgac tagtggagtt 4800
ccgcgttaca taacttacgg taaatgcccc gcctggctga ccgccaacg acccccgccc 4860
attgacgtca ataatgacgt atgttcccat agtaacgcca atagggactt tccattgacg 4920
tcaatgggtg gagtatttac ggtaaactgc ccacttggca gtacatcaag tgtatcatat 4980
gccaagtacg cccccattg acgtcaatga cggtaaatgg cccgcctggc attatgccca 5040
gtacatgacc ttatgggact ttcctacttg gcagtacatc tacgtattag tcatcgctat 5100
taccatggtc gaggtgagcc cacgttctg cttcactctc cccatctccc ccccctcccc 5160
accccccaatt ttgtatttat ttatttttta attatttttgt gcagcgatgg gggcgggggg 5220
gggggggggc gcgcgccagg cggggcgggg cgggcgaggc ggcggggcgg ggcgaggcgg 5280
agaggtgcgg cggcagccaa tcagagcggc gcgctccgaa agtttccttt tatggcggga 5340
cggcggcggc ggcggcccta taaaaagcga agcgcgcggc gggcgggagt cgctgcgcgc 5400
tgccttcgcc ccgtgcccg ctccgccgcc gcctcgcgcc gcccgcccg gctctgactg 5460
accgcgttac taaaacaggt aagtccggcc tccgcgccgg gttttggcgc ctcccgcggg 5520
cgcccccctc ctcacggcga gcgctgccac gtcagacgaa gggcgcagcg agcgtcctga 5580
tccttccgcc cggacgctca ggacagcggc ccgctgctca taagactcgg ccttagaacc 5640
ccagtatcag cagaaggaca ttttaggacg ggacttgggt gactctaggg cactggtttt 5700
cttttccagag agcggaacag gcgaggaaaa gtagtcccct ctcggcgatt ctgcggaggg 5760
atctccgtgg ggcggtgaac gccgatgatg cctctactaa ccatgttcat gttttctttt 5820
tttttctaca ggtcctgggt gacgaacagg gtaccgccac catgagggc atgaagctgc 5880
tgggggcgct gctggcactg gcggccctac tgcagggggc cgtgtcc      5927

SEQ ID NO: 2        moltype = DNA   length = 1915
FEATURE             Location/Qualifiers
source              1..1915
                    mol_type = other DNA
                    organism = synthetic construct
SEQUENCE: 2
atggatagca gcgcggcgcc gaccaacgcg agcaactgca ccgatgcgct ggcgtatagc  60
agctgcagcc cggcgccgag cccgggcagc tgggtgaacc tgagccatct ggatggcaac 120
ctgagccgatc cgtgcggccc gaaccgcacc gatctgggcg gccgcgatag cctgtgcccg 180
ccgaccgggca gcccgagcat gattaccgcg attaccatta tggcgctgaa tagcattgtg 240
tgcgtggtgg gcctgtttgg caactttctg tgatgtatg tgattgtgcg ctataccaaa 300
atgaaaaccg cgaccaacat ttatatttt aacctggcgc tggcggatgc gctggcgacc 360
agcaccctgc cgtttcagag cgtgaactat ctgatggcca cctggccgtt tggcaccatt 420
ctgtgcaaaa ttgtgattag cattgattat tataacatgt ttaccagcat ttttacccg 480
tgcaccatga gcgtggatcg ctatattgcg gtgtgccatc cggtgaaagc gctgattttt 540
cgcacccgc gcaacgcgaa aattattaac gtgtgcaact ggattctgag cagcgcgatt 600
ggcctgccgg tgatgtttat ggcgaccacc aaatatcgcc agggcagcat tgattgcacc 660
ctgaccttta gccatccgac ctggtattgg gaaaacctgc tgaaaatttg cgtgtttatt 720
tttgcgttta ttatgccggt gctgattatt accgtgtgct atggcctgat gattctgcgc 780
ctgaaaagcg tgccgcatgc tgagcggcagc aagaaaaag atcgcaacct gcgcaaaatt 840
acccgcatgg tgctggtggt ggtggcggtg tttattgtgt gctggaccc gattcatatt 900
tatgtgatta ttaaagcgct ggtgaccatt ccggaaacca ccttcagac cgtgagctgg 960
cattttgca ttgcgctggg ctataccaac agctgcctga acccggtgct gtatgcgttt 1020
ctggatgaaa actttaaacg ctgctttcgc gaattttgca ttccgaccag cagcaacatt 1080
gaacagcaga acagcacccg cattcgccag aacacccgcg atcatccgag caccgcgaac 1140
accgtggatc gcaccaacca tcagctggaa aacctggaag cggaaaccgc gccgctgccg 1200
gggcggatca gcggatcac ccaaatcttg tgacaaaact cacacatgcc caccgtgccc 1260
agcacctgaa ctcctggggg gaccgtcagt cttcctcttc cccccaaaac ccaaggacac 1320
cctcatgatc tcccggaccc ctgaggtcac atgcgtggtg gtggacgtga gccacgaaga 1380
ccctgaggtc aagttcaact ggtacgtgga cggcgtggag gtgcataatg ccaagacaaa 1440
gccgcgggag gagcagtaca acagcacgta ccgtgtggtc agcgtcctca ccgtcctgca 1500
ccaggactgg ctgaatggca aggagtacaa gtgcaaggtc tccaacaaag ccctcccagc 1560
ccccatcgag aaaaccatct ccaaagccaa agggcagccc cgagaaccac aggtgtacac 1620
cctgcccca tcccgggagg agatgaccaa gaaccaggtc agcctgacct gcctggtcaa 1680
aggcttctat cccagcgaca tcgccgtgga gtgggagagc aatgggcagc cggagaacaa 1740
ctacaagacc acgcctcccg tgctggactc cgacggctcc ttcttcctct acagcaagct 1800
caccgtggac aagagcaggt ggcagcaggg gaacgtcttc tcatgctccg tgatgcatga 1860
ggctctgcac aaccactaca cgcagaagag cctctccctg tctccgggta aatag       1915

SEQ ID NO: 3        moltype = DNA   length = 7842
FEATURE             Location/Qualifiers
source              1..7842
                    mol_type = other DNA
                    organism = synthetic construct
SEQUENCE: 3
ttctagaata atcaacctct ggattacaaa atttgtgaaa gattgactgg tattcttaac  60
tatgttgctc cttttacgct atgtggatac gctgctttaa tgcctttgta tcatgctatt 120
gcttcccgta tggctttcat tttctcctcc ttgtataaat cctggttgct gtctctttat 180
gaggagttgt ggcccgttgt caggcaacgt ggcgtggtgt gcactgtgtt tgctgacgca 240
acccccactg gttggggcat tgccaccacc tgtcagctcc tttccgggac tttcgctttc 300
ccctccccta ttgccacggc ggaactcatc gccgcctgcc ttgcccgctg ctggacaggg 360
gctcggctgt tgggcactga caattccgtg gtgttgtcgg ggaaatcatc gtccttttcct 420
tggctgctcg cctgtgttgc cacctggatt ctgcgcggga cgtccttctg ctacgtccct 480
tcggccctca atccagcgga ccttcctttcc cgcggcctgc tgccggctct gcggcctctt 540
```

```
ccgcgtcttc gccttcgccc tcagacgagt cggatctccc tttgggccgc ctccccgcct   600
aagcttatcg ataccgtcga gatctaactt gtttattgca gcttataatg gttacaaata   660
aagcaatagc atcacaaatt tcacaaataa agcatttttt tcactgcatt ctagttgtgg   720
tttgtccaaa ctcatcaatg tatcttatca tgtctggatc tcgacctcga ctagagcatg   780
gctacgtaga taagtagcat ggcgggttaa tcattaacta caaggaaccc ctagtgatgg   840
agttggccac tccctctctg cgcgctcgct cgctcactga ggccgggcga ccaaaggtcg   900
cccgacgccc gggctttgcc cgggcggcct cagtgagcga gcgagcgcgc agctggcgt   960
aatagcgaag aggcccgcac cgatcgccct tcccaacagt tgcgcagcct gaatggcgaa  1020
tggaattcca gacgattgag cgtcaaaatg taggtatttc catgagcgtt tttcctgttg  1080
caatggctgg cggtaatatt gttctggata ttaccagcaa ggccgatagt ttgagttctt  1140
ctactcaggc aagtgatgtt attactaatc aaagaagtat tgcgacaacg gttaatttgc  1200
gtgatggaca gactctttta ctcggtggcc tcactgatta taaaaacact tctcaggatt  1260
ctggcgtacc gttcctgtct aaaatccctt aatcggcct cctgtttagc tcccgctctg   1320
attctaacga ggaaagcacg ttatacgtgc tcgtcaaagc aaccatagta cgcgccctgt  1380
agcggcgcat taagcgcggc gggtgtggtg gttacgcgca gcgtgaccgc tacacttgcc  1440
agcgccctag cgcccgctcc tttcgctttc ttcccttcct ttctcgccac gttcgccggc  1500
tttccccgtc aagctctaaa tcgggggctc cctttagggt tccgatttag tgctttacgg  1560
cacctcgacc ccaaaaaact tgattagggt gatggttcac gtagtgggcc atcgccctga  1620
tagacggttt ttcgcccttt gacgttggag tccacgttct ttaatagtgg actcttgttc  1680
caaactggaa caacactcaa ccctatctcg gtctattctt ttgatttata agggattttg  1740
ccgatttcgg cctattggtt aaaaaatgag ctgatttaac aaaaatttaa cgcgaatttt  1800
aacaaaatat taacgtttac aatttaaata tttgcttata caatcttcct gtttttgggg  1860
cttttctgat tatcaaccgg ggtacatatg attgacatgc tagttttacg attaccgttc  1920
atcgattctc ttgtttgctc cagactctca ggcaatgacc tgatagcctt tgtagagacc  1980
tctcaaaaat agctaccctc tccggcatga atttatcagc tagaacggtt gaatatcata  2040
ttgatggtga tttgactgtc tccggccttt ctcacccgtt tgaatctttta cctacacatt  2100
actcaggcat tgcatttaaa atatatgagg gttctaaaaa ttttttatcct tgcgttgaaa  2160
taaaggcttc tcccgcaaaa gtattacagg gtcataatgt ttttggtaca accgatttag  2220
ctttatgctc tgaggcttta ttgcttaatt ttgctaattc tttgccttgc ctgtatgatt  2280
tattggatgt tggaattcct gatgcggtat tttctcctta cgcatctgtg cggtatttca  2340
caccgcatat ggtgcactct cagtacaatc tgctctgatg ccgcatagtt aagccagccc  2400
cgacacccgc caacacccgc tgacgcgccc tgacgggctt gtctgctccc ggcatccgct  2460
tacagacaag ctgtgaccgt ctccgggagc tgcatgtgtc agaggttttc accgtcatca  2520
ccgaaacgcg cgagacgaaa gggcctcgtg atacgcctat ttttataggt taatgtcatg  2580
ataataatgg tttcttagac gtcaggtggc acttttcggg gaaatgtgcg cggaacccct  2640
atttgtttat ttttctaaat acattcaaat atgtatccgc tcatgagaca ataaccctga  2700
taaatgcttc aataatattg aaaaaggaag agtatgagta ttcaacattt ccgtgtcgcc  2760
cttattccct ttttttgcggc attttgcctt cctgtttttg ctcacccaga aacgctggtg  2820
aaagtaaaag atgctgaaga tcagttgggt gcacgagtgg gttacatcga actggatctc  2880
aacagcggta agatcttga gagttttcgc cccgaagaac gttttccaat gatgagcact  2940
tttaaagttc tgctatgtgg cgcggtatta cccgtattg acgccgggca agagcaactc  3000
ggtcgccgca tacactattc tcagaatgac ttggttgagt actcaccagt cacagaaaag  3060
catcttacgg atggcatgac agtaagagaa ttatgcagtg ctgccataac catgagtgat  3120
aacactgcgg ccaacttact tctgacaacg atcggaggac cgaaggagct aaccgctttt  3180
ttgcacaaca tgggggatca tgtaactcgc cttgatcgtt gggaaccgga gctgaatgaa  3240
gccataccaa acgacgagcg tgacaccacg atgcctgtag caatggcaac aacgttgcgc  3300
aaactattaa ctggcgaact acttactcta gcttcccggc aacaattaat agactggatg  3360
gaggcggata aagttgcagg accacttctg cgctcggccc ttccggctgg ctggtttatt  3420
gctgataaat ctggagccgg tgagcgtggg tctcgcggta tcattgcagc actggggcca  3480
gatggtaagc cctcccgtat cgtagttatc tacacgacgg ggagtcaggc aactatggat  3540
gaacgaaata gacagatcgc tgagataggt gcctcactga ttaagcattg gtaactgtca  3600
gaccaagttt actcatatat actttagatt gatttaaaac ttcatttta atttaaaagg  3660
atctaggtga agatccttt tgataatctc atgaccaaaa tcccttaacg tgagttttcg  3720
ttccactgag cgtcagaccc cgtagaaaag atcaaaggat cttcttgaga tccttttttt  3780
ctgcgcgtaa tctgctgctt gcaaacaaaa aaaccaccgc taccagcggt ggtttgtttg  3840
ccggatcaag agctaccaac tctttttccg aaggtaactg gcttcagcag agcgcagata  3900
ccaaatactg tccttctagt gtagccgtag ttaggccacc acttcaagaa ctctgtagca  3960
ccgcctacat acctcgctct gctaatcctg ttaccagtgg ctgctgccag tggcgataag  4020
tcgtgtctta ccgggttgga ctcaagacga tagttaccgg ataaggcgca gcggtcgggc  4080
tgaacggggg gttcgtgcac acagcccagc ttggagcgaa cgacctacac gaactgagat  4140
acctacagcg tgagctatg agaaagcgcc acgcttcccg aagggagaaa ggcggacagg  4200
tatccggtaa gcggcaggt cggaacagga gagcgcacga gggagcttcc agggggaaac  4260
gcctggtatc tttatagtcc tgtcgggttt cgccacctct gacttgagcg tcgatttttg  4320
tgatgctcgt caggggggcg gagcctatgg aaaaacgcc agcaacgcgg cctttttacg  4380
ttcctggcct tttgctggcc ttttgctcac atgttctttc ctgcgttatc ccctgattct  4440
gtggataacc gtattaccgc ctttgagtga gctgataccg ctcgccgcag ccgaacgacc  4500
gagcgcagcg agtcagtgag cgaggaagcg gaagagcgcc caatacgcaa accgcctctc  4560
cccgcgcgtt ggccgattca ttaatgcagc agctgcgcgc tcgctcgctc actgaggccg  4620
cccgggcaaa gcccgggcgt cgggcgacct tggtccgcagtg agcgagcgag  4680
cgcgcagaga gggagtggcc aactccatca ctaggggttc cttgtagtta atgattaacc  4740
cgccatgcta cttatctacg tagccatgct ctaggacatt gattattgac tagtggagtt  4800
ccgcgttaca taacttacgg taaatggccc gcctggctga cgcccaacg acccccgccc  4860
attgacgtca ataatgacgt atgttcccat agtaacgcca atagggactt tccattgacg  4920
tcaatgggtg gagtatttac ggtaaactgc ccacttggca gtacatcaag tgtatcatat  4980
gccaagtacg ccccctattg acgtcaatga cggtaaatgg cccgcctggc attatgccca  5040
gtacatgacc ttatgggact ttcctacttg gcagtacatc tacgtattag tcatcgctat  5100
taccatggtc gaggtgagcc ccacgttctg cttcactctc cccatctccc cccctcccc   5160
acccccaatt ttgtatttat ttattttta attattttgt gcagcgatgg gggcggggggg  5220
ggggggggc gcgcgccagg cggggcgggg cggggcgagg ggcggggcgg ggcgaggcgg  5280
```

```
agaggtgcgg cggcagccaa tcagagcggc gcgctccgaa agtttccttt tatggcgagg    5340
cggcggcggc ggcggcccta taaaaagcga agcgcgcggc gggcgggagt cgctgcgcgc    5400
tgccttcgcc ccgtgccccg ctccgccgcc gcctcgcgcc gcccgccccg gctctgactg    5460
accgcgttac taaaacaggt aagtccggcc tccgcgccgg gttttggcgc ctcccgcggg    5520
cgcccccctc ctcacggcga gcgctgccac gtcagacgaa gggcgcagcg agcgtcctga    5580
tccttccgcc cggacgctca ggacagcggc ccgctgctca taagactcgg ccttagaacc    5640
ccagtatcag cagaaggaca ttttaggacg ggacttgggt gactctaggg cactggtttt    5700
ctttccagag agcggaacag gcgaggaaaa gtagtccctt ctcggcgatt ctgcggaggg    5760
atctccgtgg ggcggtgaac gccgatgatg cctctactaa ccatgttcat gttttctttt    5820
tttttctaca ggtcctgggt gacgaacagg gtaccgccac catgagggc atgaagctgc    5880
tgggggcgct gctggcactg gcggcctac tgcaggggc cgtgtccatg gatagcagcg    5940
cggcgccgac caacgcgagc aactgcaccg atgcgctggc gtatagcagc tgcagcccgg    6000
cgccgagccc gggcagctgg gtgaacctga gccatctgga tggcaacctg agcgatccgt    6060
gcggcccgaa ccgcaccgat ctgggcggcc gcgatagcct gtgcccgccg accggcagcc    6120
cgagcatgat taccgcgatt accattatgt cgctgtatag cattgtgtgc gtggtgggcc    6180
tgtttatggc ctttctggtg atgtatgtga ttgtgcgcta taccaaaatg aaaaccgcga    6240
ccaacattta tattttaac ctggcgctgg cggatgcgct ggcgaccagc accctgccgt    6300
ttcagagcgt gaactatctg atgggcacct ggccgtttgg caccattctg tgcaaaattg    6360
tgattagcat tgattattat aacatgttta ccagcatttt taccctgtgc accatgagcg    6420
tggatcgcta tattgcggtg tgccatccgg tgaaagcgct ggattttcgc accccgcgca    6480
acgcgaaaat tattaacgtg tgcaactgga ttctgagcag cgcgattggc ctgccggtga    6540
tgtttatggc gaccaccaaa tatcgccagg gcagcattga ttgcacccctg accttagcc    6600
atccgacctg gtattgggaa aacctgctga aaatttgcgt gtttatttt gcgtttatta    6660
tgccggtgct gattattacc gtgtgctatg gcctgatgat tctgcgcctg aaaagcgtgc    6720
gcatgctgag cggcagcaaa gaaaaagatc gcaacctgcg caaaattacc cgcatggtgc    6780
tggtggtggt ggcggtgttt attgtgtgct ggacccgat tcatatttat gtgattatta    6840
aagcgctggt gaccattccg gaaaccacct ttcagaccgt gagctggcat ttttgcattg    6900
cgctgggcta taccaacagc tgcctgaacc cggtgctgta tgcgtttctg gatgaaaact    6960
ttaaacgctg ctttcgcgaa ttttgcattc cgaccagcag caacattgaa cagcagaaca    7020
gcacccgcat tcgccagaac acccgcgatc atccgacgac cgcgaaccgc gtggatcgca    7080
ccaaccatca gctggaaaac ctggaagcgg aaaccgcgcc gctgccgggg cggatcaggc    7140
ggatcaccca aatcttgtga caaaactcac acatgcccac cgtgcccagc acctgaactc    7200
ctgggggac cgtcagtctt cctcttcccc ccaaaaccca aggacaccct catgatctcc    7260
cggacccctg aggtcacatg cgtggtggtg gacgtgagcc acgaagaccc tgaggtcaag    7320
ttcaactggt acgtggacgg cgtggaggtg cataatgcca agacaaagcc gcgggaggag    7380
cagtacaaca gcacgtaccg tgtggtcagc gtcctcaccg tcctgcacca ggactggctg    7440
aatggcaagg agtacaagtg caaggtctcc aacaaagccc tcccagcccc catcgagaaa    7500
accatctcca aagccaaagg gcagccccga gaaccacagg tgtacaccct gcccccatcc    7560
cgggaggaga tgaccaagaa ccaggtcagc ctgacctgcc tggtcaaagg cttctatccc    7620
agcgacatcg ccgtggagtg ggagagcaat gggcagccgg agaacaacta caagaccacg    7680
cctcccgtgc tggactccga cggctccttc ttcctctaca gcaagctcac cgtggacaag    7740
agcaggtggc agcaggggaa cgtcttctca tgctccgtga tgcatgaggc tctgcacaac    7800
cactacacgc agaagagcct ctccctgtct ccgggtaaat ag                      7842
```